US010932653B2

(12) United States Patent
Okaniwa et al.

(10) Patent No.: US 10,932,653 B2
(45) Date of Patent: Mar. 2, 2021

(54) ENDOSCOPE SYSTEM (71) Applicant: OLYMPUS CORPORATION, Tokyo (JP)

(72) Inventors: Suguru Okaniwa, Hachioji (JP); Seisuke Takase, Hachioji (JP); Hidehiro Joko, Hachioji (JP); Isamu Nakajima, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 428 days.

(21) Appl. No.: 15/706,682

(22) Filed: Sep. 16, 2017

(65) Prior Publication Data

US 2018/0000325 A1 Jan. 4, 2018

Related U.S. Application Data

(63) Continuation of application No. PCT/JP2016/084766, filed on Nov. 24, 2016.

(30) Foreign Application Priority Data

Nov. 24, 2015 (JP) .............................. JP2015-228969

(51) Int. Cl.
*A61B 1/00* (2006.01)
*G02B 23/24* (2006.01)
*A61B 1/005* (2006.01)

(52) U.S. Cl.
CPC ........ *A61B 1/00135* (2013.01); *A61B 1/0014* (2013.01); *A61B 1/0051* (2013.01);
(Continued)

(58) Field of Classification Search
CPC ............ A61B 1/00135; A61B 1/00078; A61B 1/00071; A61B 1/0014; A61B 1/00154;
(Continued)

(56) References Cited

U.S. PATENT DOCUMENTS 5,885,208 A 3/1999 Moriyama
2008/0249356 A1* 10/2008 Motai ................ A61B 1/00082
600/114

(Continued)

FOREIGN PATENT DOCUMENTS

JP 9-108176 A 4/1997
JP 2004-121860 A 4/2004

OTHER PUBLICATIONS

International Search Report dated Feb. 14, 2017 received in PCT/JP2016/084766.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

Maximum hardness of a flexible tube section of an endoscope is set such that substantial maximum hardness at a time when an over-tube is attached is equal to or lower than maximum hardness of a flexible tube section of an endoscope. That is, the maximum hardness of the flexible tube section of the endoscope is set substantially equal to hardness obtained by subtracting hardness of the over-tube itself from the maximum hardness of the flexible tube section of the endoscope. In the endoscopes including a hardness changing mechanism, maximum hardness of the endoscope, to which the over-tube is not attached, and maximum hardness of the endoscope, to which the over-tube is attached, are set substantially equal.

3 Claims, 8 Drawing Sheets

(52) U.S. Cl.
CPC ...... *A61B 1/00078* (2013.01); *A61B 1/00154* (2013.01); *G02B 23/24* (2013.01)

(58) Field of Classification Search
CPC ... A61B 1/0051; A61B 1/005; A61B 17/3417; A61B 1/00105; A61B 1/00101; A61B 1/00142; A61B 1/273; A61B 1/2733; A61B 1/2736; A61B 1/2676; A61B 1/31; A61B 1/00082; A61B 25/0062; G02B 23/24; A61M 2025/0024–0025; A61M 2025/0687; A61M 2025/0681; A61M 25/0662
USPC .................. 600/114, 128, 139, 144, 146
See application file for complete search history.

(56) References Cited

U.S. PATENT DOCUMENTS

| | | | |
|---|---|---|---|
| 2011/0046442 A1* | 2/2011 | Matsushita | A61B 1/00071 600/114 |
| 2012/0053417 A1* | 3/2012 | Yamakawa | A61B 1/00066 600/144 |
| 2012/0071722 A1* | 3/2012 | Nakamura | A61B 1/00078 600/140 |
| 2012/0184817 A1* | 7/2012 | Sugiyama | A61B 1/00154 600/114 |
| 2014/0039259 A1* | 2/2014 | Okaniwa | A61B 1/005 600/139 |

* cited by examiner

ENDOSCOPE SYSTEM

CROSS REFERENCE TO RELATED APPLICATION

This application is a continuation application of PCT/JP2016/084766 filed on Nov. 24, 2016 and claims benefit of Japanese Application No. 2015-228969 filed in Japan on Nov. 24, 2015, the entire contents of which are incorporated herein by this reference.

BACKGROUND OF THE INVENTION

1. Field of the Invention

The present invention relates to an endoscope system including an endoscope to which an over-tube is attachable and an endoscope to which the over-tube is un-attachable.

2. Description of the Related Art

In recent years, an endoscope has been widely used that makes it possible to observe an inspection target part in a subject by inserting an elongated insertion section into the subject and enables curative treatment in which a treatment instrument is used, as necessary.

The insertion section of the endoscope is configured by coupling a flexible tube having flexibility to a rigid portion at a distal end such that the insertion section can be inserted into even a bent insertion path.

Also, there has been proposed an endoscope including a hardness changing mechanism (hardness variable means) that incorporates, on an inside of the flexible tube, a pipe-like coil and a wire for towing the coil and can change hardness of the flexible tube by towing the wire and compressing the coil.

For example, Japanese Patent Application Laid-Open Publication No. 2004-121860 discloses an endoscope system including a plurality of endoscopes having different insertion section lengths, the endoscope system including, in flexible portions of the endoscopes, hardness variable means that increases hardness according to a bending amount in a hard state.

In general, in a medical examination in which an endoscope is used, an optimum endoscope is selected and an insertion operation method is different according to sex and various body shapes of a patient, presence or absence of adhesion, or the like. An over-tube, which is an insertion supporting instrument, is sometimes used together with the endoscope.

SUMMARY OF THE INVENTION

An endoscope system according to an aspect of the present invention is an endoscope system including: a first endoscope including a first insertion section formed to be elongated and a first hardness changing mechanism configured to change hardness of the first insertion section according to operation on a hand side; and a second endoscope including a second insertion section formed to be elongated and a second hardness changing mechanism configured to change hardness of the second insertion section according to operation on the hand side, an over-tube being attachable to an outer circumference of the second insertion section, the first endoscope and the second endoscope being selectively usable. Maximum hardness in the second insertion section of the second endoscope in a state in which the over-tube is attached is set substantially equal to maximum hardness in the first insertion section of the first endoscope.

An endoscope system according to another aspect of the present invention includes: a first endoscope including a first insertion section, a first repulsive force of which is applied to a hand of a surgeon when being inserted into a predetermined position of a subject; a second endoscope including a second insertion section, a second repulsive force of which larger than the first repulsive force is applied to the hand of the surgeon when being inserted into the predetermined position of the subject; an over-tube configured to enable the first insertion section to be inserted through an inside, hardness of the over-tube being set such that a third repulsive force applied to the hand of the surgeon when the first insertion section is inserted into the subject in a state in which the first insertion section is inserted through the inside is substantially equal to the second repulsive force.

DETAILED DESCRIPTION OF THE PREFERRED EMBODIMENT(S)

Embodiments of the present invention are explained below with reference to the drawings.

First Embodiment

Figure 1:
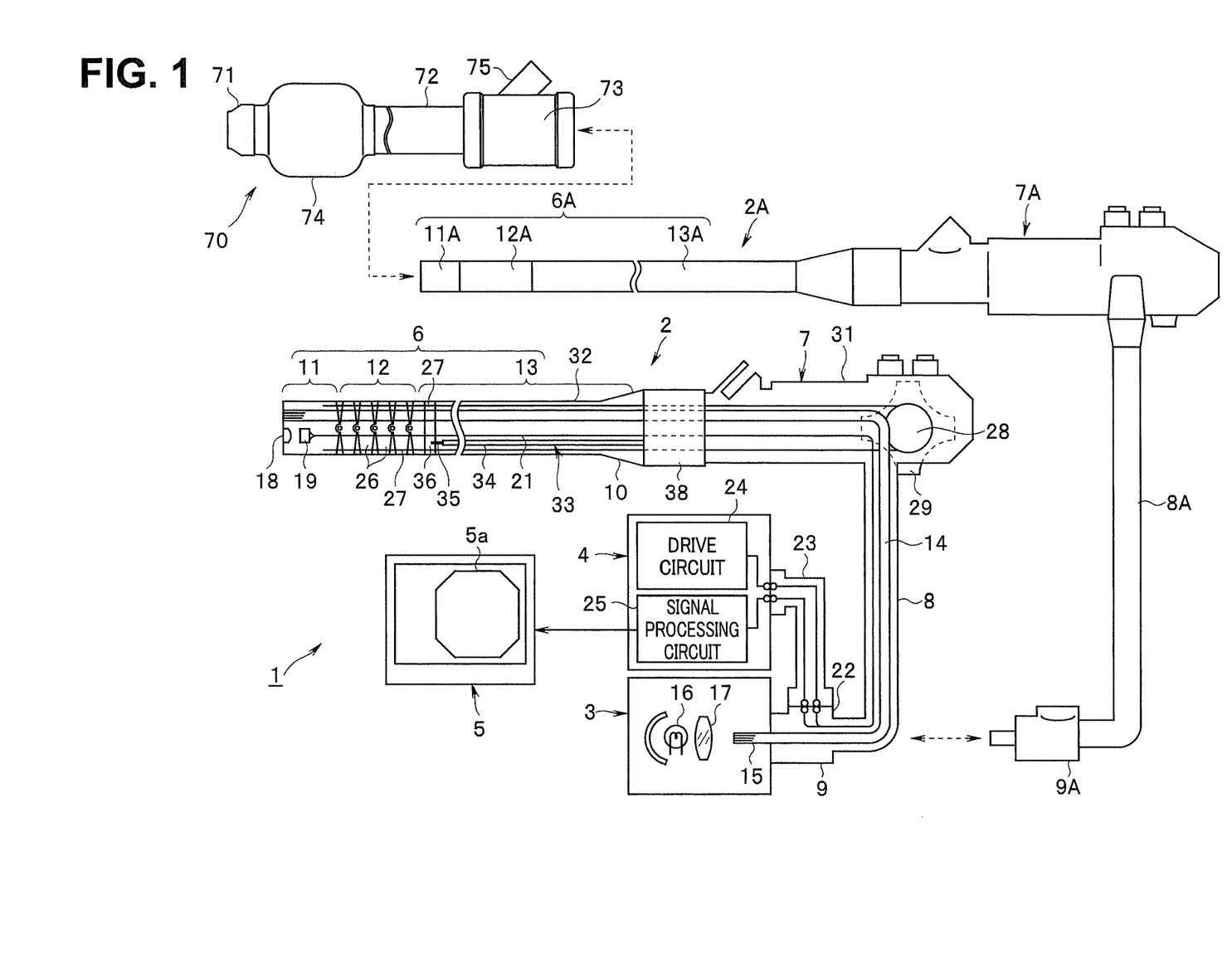
FIG. 1 relates to a first embodiment of the present invention and is a schematic configuration diagram of an endoscope system.

An endoscope system 1 shown in FIG. 1 includes a first endoscope 2, a second endoscope 2A, an over-tube 70, which is an insertion supporting instrument, attached to the second endoscope 2A, a light source device 3 configured to supply illumination light to the first endoscope 2 or the second endoscope 2A, a signal processing device 4 configured to perform signal processing of an image-pickup signal outputted from the first endoscope 2 or the second endoscope 2A, and a monitor 5 configured to display a video signal outputted from the signal processing device 4 on a screen.

The first endoscope 2 and the second endoscope 2A (hereinafter simply described as "endoscope 2" and "endoscope 2A") have the same basic configuration and respectively include an elongated first insertion section 6 and an elongated second insertion section 6A (hereinafter simply described as "insertion section 6" and "insertion section 6A"). As explained below, the endoscopes 2 and 2A respectively include first and second hardness changing mechanisms configured to change hardness (flexibility) of the insertion sections. In the following explanation, the endoscopes 2 and 2A are represented by the endoscope 2 and the configuration of the endoscope 2 is explained.

The endoscope 2 includes the elongated insertion section 6, a wide operation section 7 concatenated on a rear end side of the insertion section 6, and a universal cable 8 extended from a side portion of the operation section 7. A connector 9 is provided at an end portion of the universal cable 8. The endoscope 2 can be detachably connected to the light source device 3 and the signal processing device 4 via the connector 9.

The insertion section 6 includes, from a distal end side, a rigid distal end portion 11, a bending section 12 formed at a rear end of the distal end portion 11 and capable of bending, and a flexible tube section 13 formed at a rear end of the bending section 12 and long and having flexibility. A rear end side of the flexible tube section 13 is coupled to a front end side of the operation section 7. A bending preventing member 10 formed in a taper shape and having a bending preventing function is provided in a rear end outer circumference of the flexible tube section 13. A cylindrical hardness adjustment knob 38 for hardness changing operation is turnably provided in a part that is a front end portion of the operation section 7 on a proximal end side of the bending preventing member 10.

Note that, in the endoscope 2A, an operation section 7A, a universal cable 8A, and a connector 9A are the same as the components of the endoscope 2. However, as explained below, the endoscope 2A is different from the endoscope 2 in an outer diameter of the insertion section 6A (a distal end portion 11A, a bending section 12A, and a flexible tube section 13A). According to the difference in the outer diameter, the over-tube 70 cannot be attached to the insertion section 6 of the endoscope 2 and can be attached to the insertion section 6A of the endoscope 2A. The endoscopes 2 and 2A are selectively connected to the light source device 3 and the signal processing device 4 via the connectors 9 and 9A and used.

A light guide 14 formed by a fiber bundle, which has flexibility and transmits illumination light, is inserted through the insertion section 6, the operation section 7, and the universal cable 8 of the endoscope 2. A proximal end portion of the light guide 14 is fixed to a light guide connector section 15 provided to project from the connector 9. By connecting the light guide connector section 15 to the light source device 3, illumination light of a lamp 16 in the light source device 3 is condensed by a lens 17 and supplied to an end face of the light guide connector section 15. Illumination light is transmitted to a distal end side of the insertion section 6 by the light guide 14.

The illumination light transmitted by the light guide 14 is emitted forward from a distal end face fixed to an illumination window of the distal end portion 11 and illuminates a subject such as a diseased part. The illuminated subject forms, with an objective lens 18 attached to an observation window provided at the distal end portion 11 adjacent to the illumination window, an optical image in an image forming position of the objective lens 18. An image pickup device 19 formed by a CCD, a CMOS, or the like is disposed in the image forming position. The optical image is converted into an electric signal.

The image pickup device 19 is connected to one end of a signal cable 21. The signal cable 21 is inserted through the insertion section 6 and the like. A rear end of the signal cable 21 is connected to an electric connector 22 of the connector 9. The signal cable 21 is connected to the signal processing device 4 via an external cable 23 connected to the electric connector 22. The signal processing device 4 generates, in a drive circuit 24, a drive signal for driving the image pickup device 19. The drive signal is applied to the image pickup device 19, whereby a photoelectrically converted image pickup signal is read out and inputted to the signal processing circuit 25 in the signal processing device 4. The signal processing circuit 25 converts the image pickup signal into a standard video signal and outputs the standard video signal to the monitor 5. The monitor 5 displays a subject image in an endoscopic image display region 5a on the basis of the inputted video signal.

The bending section 12 provided adjacent to the distal end portion 11 is configured by turnably coupling a ring-shaped large number of bending pieces 26 to adjacent bending pieces 26 in positions corresponding to top and bottom and left and right by rivets and the like. A bending operation wire 27 is fixed to the bending piece 26 at a most distal end or the distal end portion 11. A rear end side of the bending operation wire 27 is coupled to a sprocket 28 in the operation section 7.

A bending operation knob 29 for performing bending operation is attached to a shaft of the sprocket 28 (in FIG. 1, for simplification, an outline of a bending mechanism in only an up-down or left-right direction is shown). One of a pair of bending operation wires 27 disposed along the up-down direction or the left-right direction is towed and the other is slacked by performing operation for turning the bending operation knob 29 to make it possible to bend the bending section 12 to the towed bending operation wire 27 side.

In the operation section 7, a grasping section 31 is provided further on a front side than a position where the bending operation knob 29 is provided. The surgeon can perform operation and the like of the bending operation knob 29 with one hand grasping (a finger such as a thumb not used for grasping of) the grasping section 31.

A hardness changing mechanism 50 configured to change hardness (flexibility) of the flexible tube section 13 configuring a proximal end side of the insertion section 6 is explained with reference to FIG. 1 and FIG. 2. Note that first and second hardness changing mechanisms of the endoscopes 2 and 2A basically have the same configuration. Therefore, the hardness changing mechanism 50 is representatively explained. However, as explained below, in the first hardness changing mechanism of the endoscope 2 and the second hardness changing mechanism of the endoscope 2A, changeable maximum hardnesses are set to be different.

The hardness changing mechanism 50 includes a hardness (flexibility) variable member 33 made of an elongated member inserted through an inside of a flexible tube 32 forming an outer skin (an overcoat) of the flexible tube section 13 and a towing mechanism 46 configured to tow and contract the hardness variable member 33. The towing mechanism 46 is provided in the operation section 7 and tows and contracts the hardness variable member 33 according to turning operation of the hardness adjustment knob 38.

More specifically, the hardness variable member 33 includes a coil pipe 34 made of metal in a pipe-like densely wound state and a flexible towing wire 35 inserted through the coil pipe 34. A distal end of the towing wire 35 is firmly fixed by brazing or the like to an inner wall of a hard and ring-shaped connection tube 36 configured to connect the bending section 12 and the flexible tube section 13.

Figure 2:
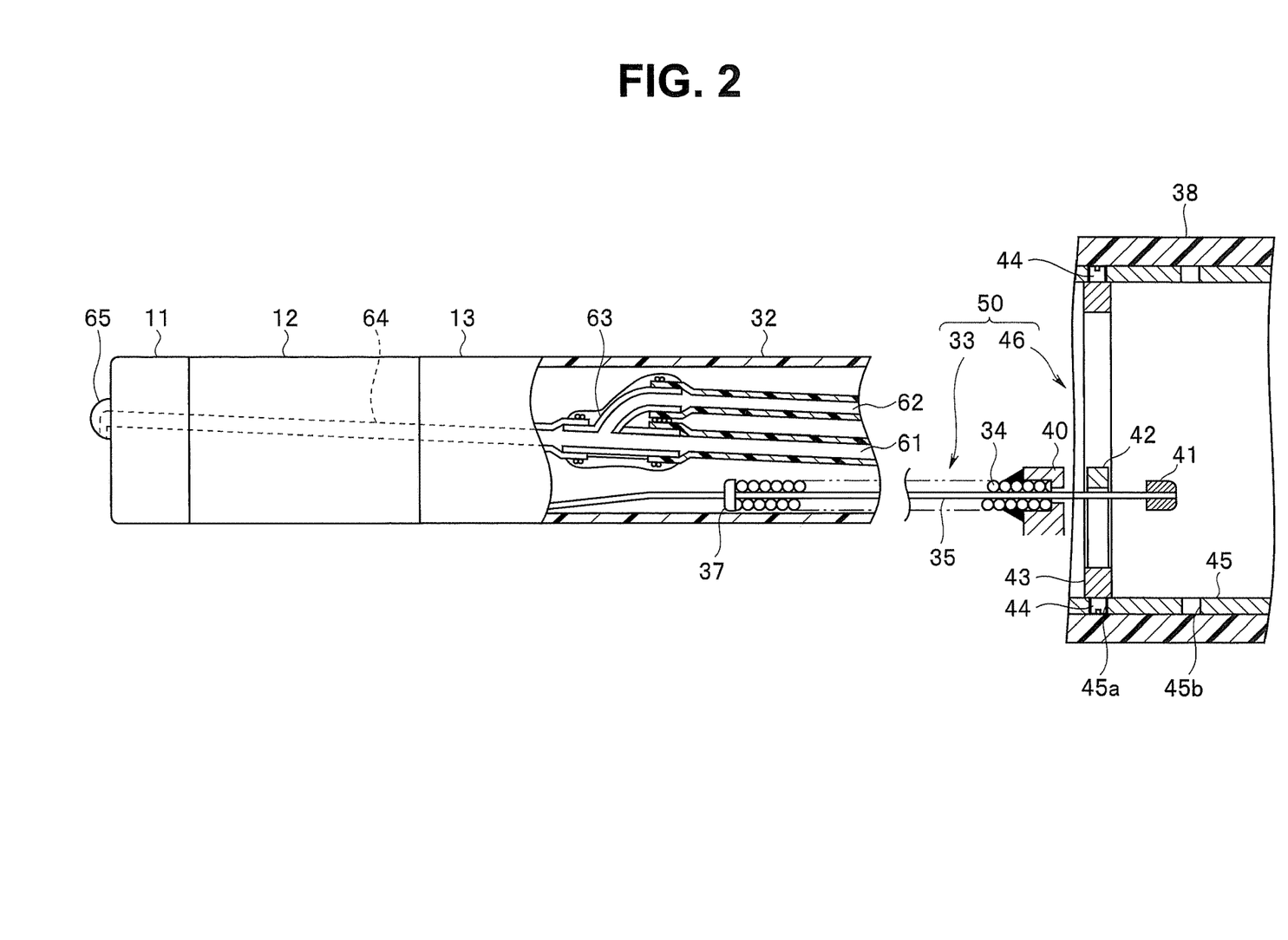
FIG. 2 relates to the first embodiment of the present invention and is an explanatory diagram showing a hardness changing mechanism of an endoscope.

As shown in FIG. 2, a distal end side of the coil pipe 34 is firmly fixed by brazing or the like to the towing wire 35 via a cap 37. A distal end of the towing wire 35 extended from the cap 37 is fixed to the connection tube 36. That is, a distal end side of the hardness variable member 33 including the coil pipe 34 and the towing wire 35 is fixed to the connection tube 36 to prevent the coil pipe 34 and the towing wire 35 from being tangled in other internal components to damage the other internal components.

Note that a distal end portion of the towing wire 35 extended from the cap 37 may be extended by fixing a wire different from the towing wire 35 to an inner side of the cap 37. A distal end of the different wire may be fixed to the connection tube 36.

On the other hand, a rear end side of the coil pipe 34 is firmly fixed by brazing or the like to a coil stopper 40 fixed to a pipe sleeve (not shown in the figure) for fixing a rear end of the flexible tube 32 to the operation section 7. The towing wire 35 inserted through the coil pipe 34 is extended to a rear side piercing through a hole provided in the coil stopper 40. An end portion on the hand side, that is, a rear end of the towing wire 35 is firmly fixed by brazing or the like to a ring-shaped wire stopper 41.

The towing mechanism 46, which tows and contracts the hardness variable member 33, is configured mainly from a towing member 42 configured to insert through the towing wire 35 between the coil stopper 40 and the wire stopper 41 and capable of moving in a front-rear direction and a cam cylinder body 45 configured to move the towing member 42 in an axial direction. In the present embodiment, the towing member 42 is fixed to an inner circumferential surface of a cylindrical moving ring 43. The moving ring 43 is engaged with a cam cylinder body 45, which is fixed to an inner side of the hardness adjustment knob 38, via two pins 44.

In the cam cylinder body 45, cam grooves 45a and 45b are spirally provided in opposed two places of a cylinder body portion of the cam cylinder body 45. The cam grooves 45a and 45b are formed in the same shape and respectively provided in symmetrical positions where the one of the cam grooves 45a and 45b overlaps a position to which the other of the cam grooves 45a and 45b is rotated 180 degrees with respect to an axis of the cam cylinder body 45.

When operation for turning the hardness adjustment knob 38 is performed and the cam cylinder body 45 is rotated, the pins 44 move in the cam grooves 45a and 45b and the towing member 42 moves backward. When the towing member 42 slightly moves, the towing member 42 hits the wire stopper 41 soon. In a state in which the wire stopper 41 is not moved to the rear side, the coil pipe 34 restricted from moving to the rear side by the coil stopper 40 is in a state of highest flexibility, that is, a state of base hardness in which the coil pipe 34 most easily bends.

When the cam cylinder body 45 further rotates and the towing member 42 moves backward, the towing wire 35 is towed and a compression force is applied to the coil pipe 34. The coil pipe 34 is hardened and the flexible tube section 13 can be hardened. That is, when the towing member 42 moves to the rear side and the rear end of the towing wire 35 simultaneously moves to the rear side, the coil stopper 40 relatively acts to press the coil pipe 34 to the front side.

That is, the compression force is applied to the coil pipe 34 by applying a force for moving the rear end of the towing wire 35 to the rear side. It is possible to change, with the compression force, the coil pipe 34 having elasticity to a state in which flexibility of the coil pipe 34 is low, that is, a hard state in which hardness (more accurately, hardness against bending) is high and the coil pipe 34 less easily bends. In this case, it is possible to adjust magnitude of the compression force to the coil pipe 34 according to a movement amount to the rear side of the wire stopper 41. Therefore, it is possible to change the flexible tube section 13 from a state of base hardness in which the flexible tube section 13 most easily bends to a state of maximum hardness in which the flexible tube section 13 most hardly bends.

An air feeding conduit 61 and a water feeding conduit 62 are inserted through the insertion section 6. The conduits 61 and 62 are merged with one air/water feeding conduit 64 via a branching member 63 in a position further on a distal end side than a distal end of the coil pipe 34. A nozzle 65 opened toward an outer surface of the objective lens 18 is provided at a distal end of the air/water feeding conduit 64. Further, besides the air feeding conduit 61 and the water feeding conduit 62, various internal components are disposed in the insertion section 6. For example, the bending operation wire 27, the light guide 14, the coil pipe 34, and the towing wire 35 guided by a guide pipe, the signal cable 21, a treatment instrument channel (not shown in the figure), and the like are disposed.

Figure 3:
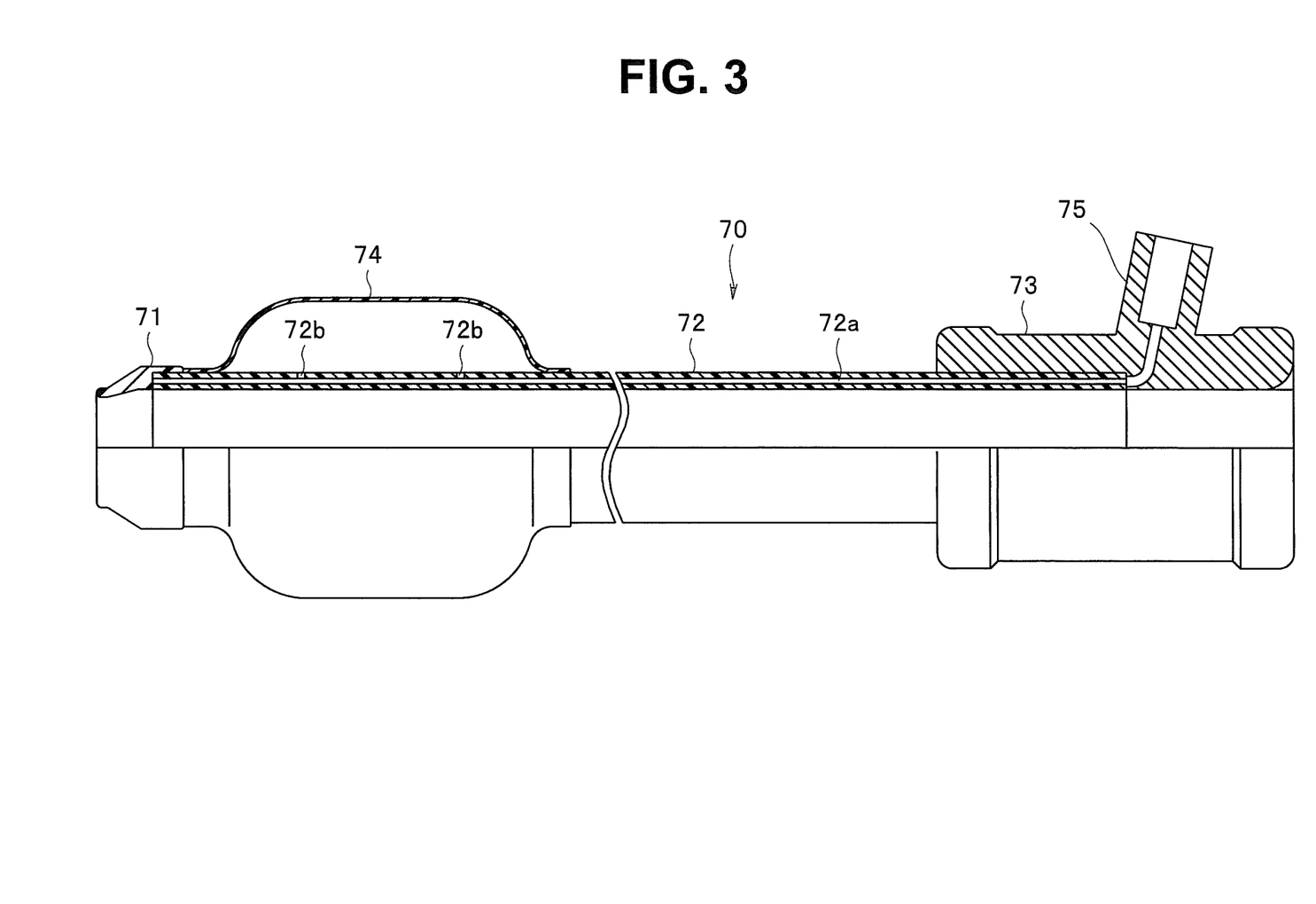
FIG. 3 relates to the first embodiment of the present invention and is a partial sectional view showing a configuration of an over-tube.

On the other hand, the over-tube 70, which is the insertion supporting instrument for the endoscope, includes, at a distal end, an annular hood 71 formed from an elastic member such as rubber, a flexible tube 72 formed of silicon or the like, to a distal end portion of which the hood 71 is bonded and fixed, and a substantially cylindrical grasping section 73 to which a proximal end portion of the flexible tube 72 is bonded and fixed.

In the present embodiment, the over-tube 70 includes a balloon 74 made of silicon or the like at a distal end portion of the flexible tube 72. As shown in FIG. 3, a conduit 72a for feeding gas to the balloon 74 is formed in a thick portion of the flexible tube 72 made of a multi-lumen tube.

In the flexible tube 72, in order to discharge the gas fed from the conduit 72a into the balloon 74 to inflate the balloon 74, a plurality of hole sections 72b communicating with the conduit 72a are formed. Further, in the grasping section 73, an air feeding pipe sleeve 75 communicating with the conduit 72a of the flexible tube 72 is disposed.

Figure 4:
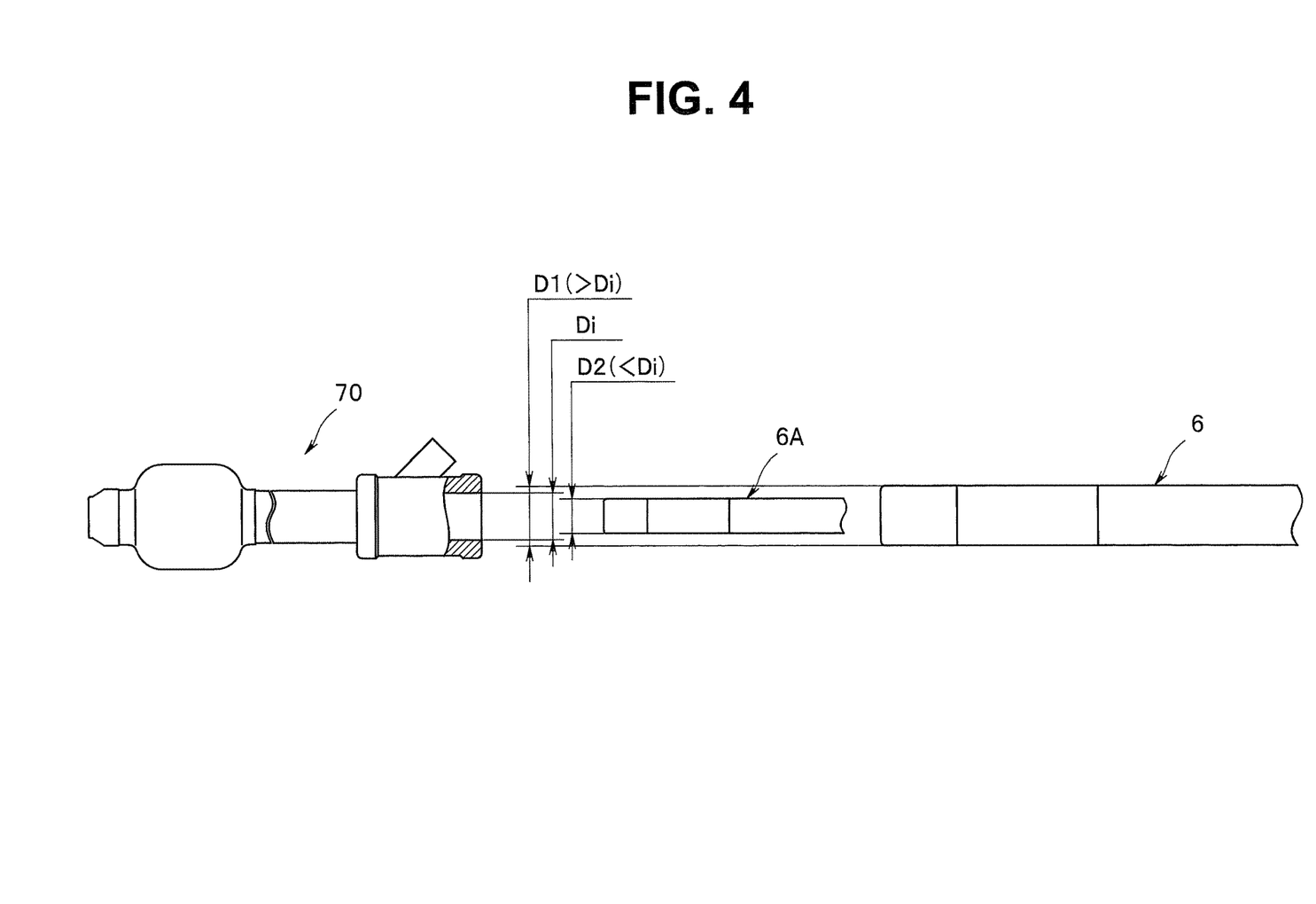
FIG. 4 relates to the first embodiment of the present invention and is an explanatory diagram showing a relation between an outer diameter of an insertion section and an inner diameter of the over-tube.

The over-tube 70 is set to be usable in combination with the endoscope 2A but unusable in combination with the endoscope 2. As shown in FIG. 4, an outer diameter D1 of the insertion section 6 of the endoscope 2 and an outer diameter D2 of the insertion section 6A of the endoscope 2A are set to be in a relation of D2<Di<D1 with respect to an inner diameter Di of the over-tube 70.

That is, in the endoscope 2A, an outer diameter of the insertion section 6A is set smaller than an inner diameter of the over-tube 70 to enable the over-tube 70 to be attached to the endoscope 2A. On the other hand, in the endoscope 2, an outer diameter of the insertion section 6 is set larger than the inner diameter of the over-tube 70 to disable the over-tube 70 to be attached to the endoscope 2.

Figure 5:
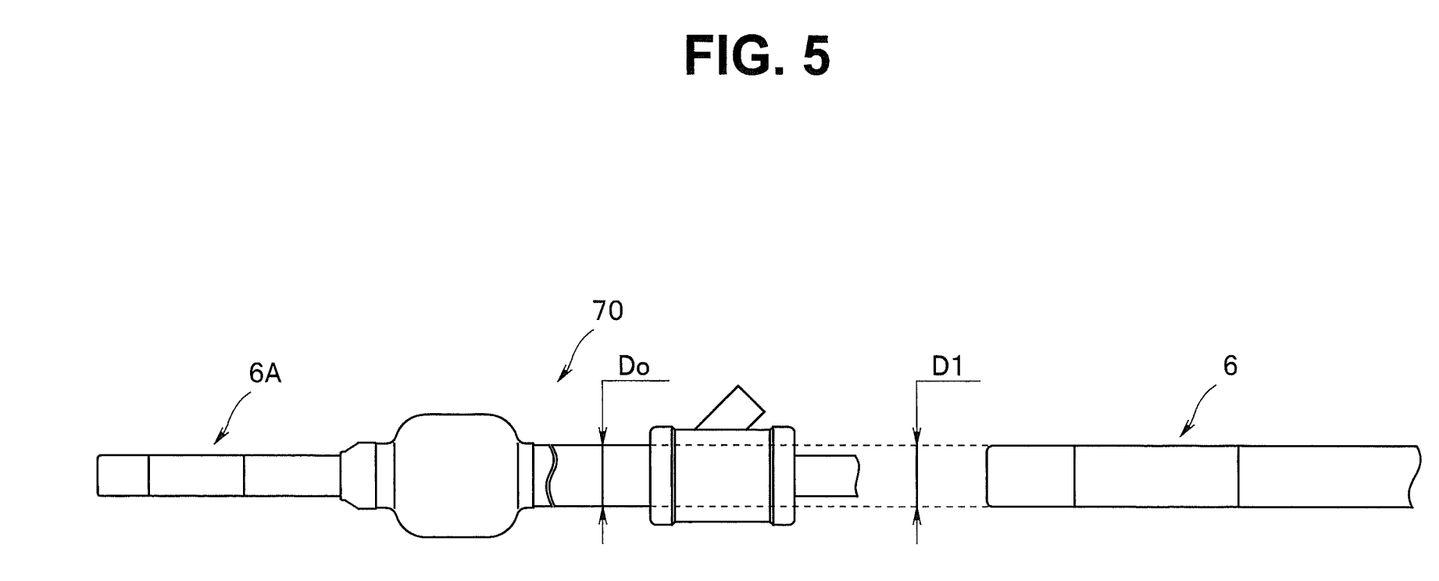
FIG. 5 relates to the first embodiment of the present invention and is an explanatory diagram showing a relation between the outer diameter of the insertion section and an outer diameter of the over-tube.

In this case, in the endoscope 2 to which the over-tube 70 cannot be attached, as shown in FIG. 5, the outer diameter D1 of the insertion section 6 may be set substantially the same as an outer diameter Do of the over-tube 70 (D1≡Do). Consequently, it is possible to set the endoscope 2A, to which the over-tube 70 is attached, and the endoscope 2, to which the over-tube 70 is not attached, to substantially the same insertion thickness and standardize convenience of use.

Subject to such a combination of the over-tube 70 and the endoscopes 2 and 2A, in the endoscope 2A in which the over-tube 70 is used, compared with the endoscope 2 in which the over-tube 70 is not used, an upper limit of a hardness change of the insertion section 6A (the flexible tube section 13A) is set lower by hardness of the over-tube 70. That is, in the endoscope 2A in which the over-tube 70 is used, maximum hardness of a portion where the over-tube 70 is attached is set substantially equal to or lower than maximum hardness of the insertion section 6 of the endoscope 2 in which the over-tube 70 is not used.

In general, in the endoscope 2 in which the over-tube 70 is not used, the maximum hardness of the insertion section 6 (maximum hardness of the flexible tube section 13) is often set within a range in which insertability into a body cavity and safety are taken into account. In such a case, when the maximum hardness in the insertion section 6A of the endoscope 2A in a state in which the over-tube 70 is attached is set the same as the maximum hardness in the insertion section 6 of the endoscope 2, substantial maximum hardness of the endoscope 2A increases by the hardness of the over-tube 70. A feeling of use is different and an unnatural feeling is given to the operator. Moreover, deterioration in insertability and an adverse effect on a human body are concerned.

Note that the feeling of use in the present invention is a feeling defined by a repulsive force felt by the surgeon in the hand when the insertion section of the endoscope is inserted into the body cavity and a predetermined amount of force necessary for inserting the insertion section into the body cavity and changing the insertion section to a predetermined bending state.

Figure 6:
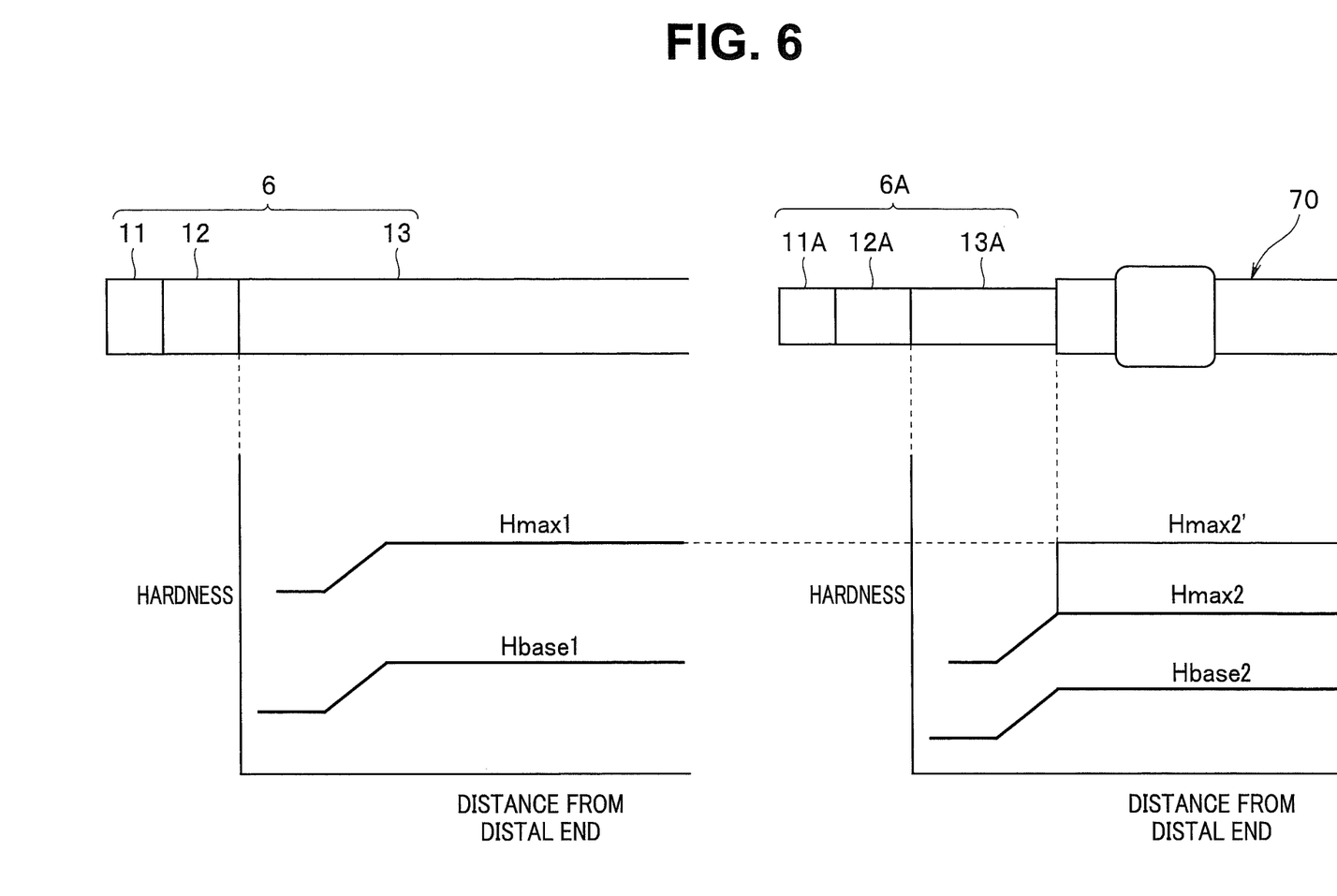
FIG. 6 relates to the first embodiment of the present invention and is an explanatory diagram showing hardness characteristics of insertion sections.

Therefore, in the present embodiment, in the endoscopes 2 and 2A, hardness characteristics by the hardness changing mechanism 50 are set to be characteristics shown in FIG. 6. FIG. 6 shows distributions of hardnesses with respect to distances of the endoscopes 2 and 2A from the distal ends of the flexible tube sections 13 and 13A and shows ranges from base hardnesses Hbase1 and Hbase2 in softest states of the flexible tube sections 13 and 13A to maximum hardnesses Hmax1 and Hmax2 in hardest states of the flexible tube sections 13 and 13A.

Note that the flexible tube sections 13 and 13A of the endoscopes 2 and 2A in the present embodiment include hardness change regions where the hardnesses gradually change from the softest state to the hardest state from flexible regions on the distal end side. As explained above, since the outer diameter of the insertion section 6 of the endoscope 2 is larger than the outer diameter of the insertion section 6A of the endoscope 2A, in general, the base hardnesses Hbase1 and Hbase2 of the endoscopes 2 and 2A are Hbase1≥Hbase2.

In the characteristics shown in FIG. 6, as the maximum hardness Hmax2 of the flexible tube section 13A of the endoscope 2A, maximum hardness Hmax2' in the state in which the over-tube 70 is attached is set equal to or lower than the maximum hardness Hmax1 of the insertion section 6 (the flexible tube section 13) of the endoscope 2. That is, the maximum hardness Hmax2 of the flexible tube section 13A of the endoscope 2A is set substantially equal to hardness obtained by subtracting the hardness of the over-tube 70 itself from the maximum hardness Hmax1 of the flexible tube section 13 of the endoscope 2. An error of the hardnesses in this case is specified to a predetermined width (e.g., 10%) with respect to a hardness variable width and a change width of hardness of the over-tube 70.

As the hardness characteristics explained above, the hardness characteristic of the endoscope 2A is set taking into account the hardness of the over-tube 70 in use on the basis of the hardness characteristic of the endoscope 2 in which the over-tube 70 is not used. For example, as explained in (1) to (4) below, it is possible to obtain the hardness characteristics shown in FIG. 6 by appropriately setting elements configuring the hardness changing mechanism of the endoscope 2A.

(1) A coil diameter of the coil pipe 34
(2) A coil element wire diameter of the coil pipe 34
(3) A wire line diameter of the towing wire 35
(4) A wire towing amount of the towing wire 35

More specifically, it is possible to reduce maximum hardness of the flexible tube section 13A of the endoscope 2A by setting the coil diameter and the coil element wire diameter of (1) and (2) and the wire line diameter of (3) in the endoscope 2A smaller than the coil diameter, the coil element wire diameter, and the wire line diameter of the endoscope 2. It is possible to reduce the maximum hardness of the flexible tube section 13A of the endoscope 2A by setting the wire towing amount of (4) in the endoscope 2A smaller than the wire towing amount of the endoscope 2.

Therefore, by adjusting conditions of (1) to (4) independently or in combination, it is possible to set the maximum hardness Hmax2 of the flexible tube section 13A of the endoscope 2A to be smaller than the maximum hardness Hmax1 of the endoscope 2A by the hardness of the over-tube 70. Further, it is possible to support the hardness adjustment by changing an outer skin of the flexible tube section 13A to a softer material.

In this way, in the present embodiment, in the endoscopes 2 and 2A including the hardness changing mechanism, the maximum hardness of the endoscope 2, to which the over-tube 70 is not attached, and the maximum hardness of the endoscope 2A, to which the over-tube 70 is attached, are set substantially equal. Consequently, it is possible to achieve the same feeling of use irrespective of presence or absence of attachment of the over-tube 70. It is possible to obtain satisfactory insertability and operability.

The endoscopes explained above include the hardness changing mechanism. However, the present invention is not limited to this. More specifically, two endoscopes having different hardnesses not including the hardness changing mechanism may be adopted. A feeling of use in a case in which the over-tube 70 is attached to a soft endoscope and a feeling of use of a hard endoscope may be set to be the same. In this case, the hardness of the over-tube 70 is set on the basis of a difference between hardness of the hard endoscope and hardness of the soft endoscope.

Note that, in the embodiment explained above, in the endoscopes 2 and 2A, the feeling of use is defined on the basis of the hardness corresponding to presence or absence of attachment of the over-tube. However, the present invention is not limited to this. More specifically, the feeling of use felt by the surgeon may be set the same by substantially equalizing a repulsive force applied to the hand of the surgeon when the endoscope 2 is inserted into a predetermined position of a subject and a repulsive force applied to the hand of the surgeon when the endoscope 2A in the state in which the over-tube is attached is inserted into the predetermined position of the subject.

Further, the feeling of use felt by the surgeon may be set the same by substantially equalizing an amount of force necessary for changing the endoscope 2 to a predetermined bending state when the endoscope 2 is inserted into the predetermined position of the subject and an amount of force necessary for changing the endoscope 2A in the state in which the over-tube is attached to a bending state substantially the same as the predetermined state when the endoscope 2A is inserted into the predetermined position of the subject.

The "repulsive force applied to the hand of the surgeon" and the "amount of force necessary for changing the endoscope to the predetermined bending state" can be measured using, for example, a measuring method for measuring flexural rigidity disclosed in Japanese Patent Application Laid-Open Publication No. 2014-083293.

Second Embodiment

A second embodiment of the present invention is explained. In the second embodiment, an endoscope not including the hardness changing mechanism is included in the endoscope system 1.

Figure 7:
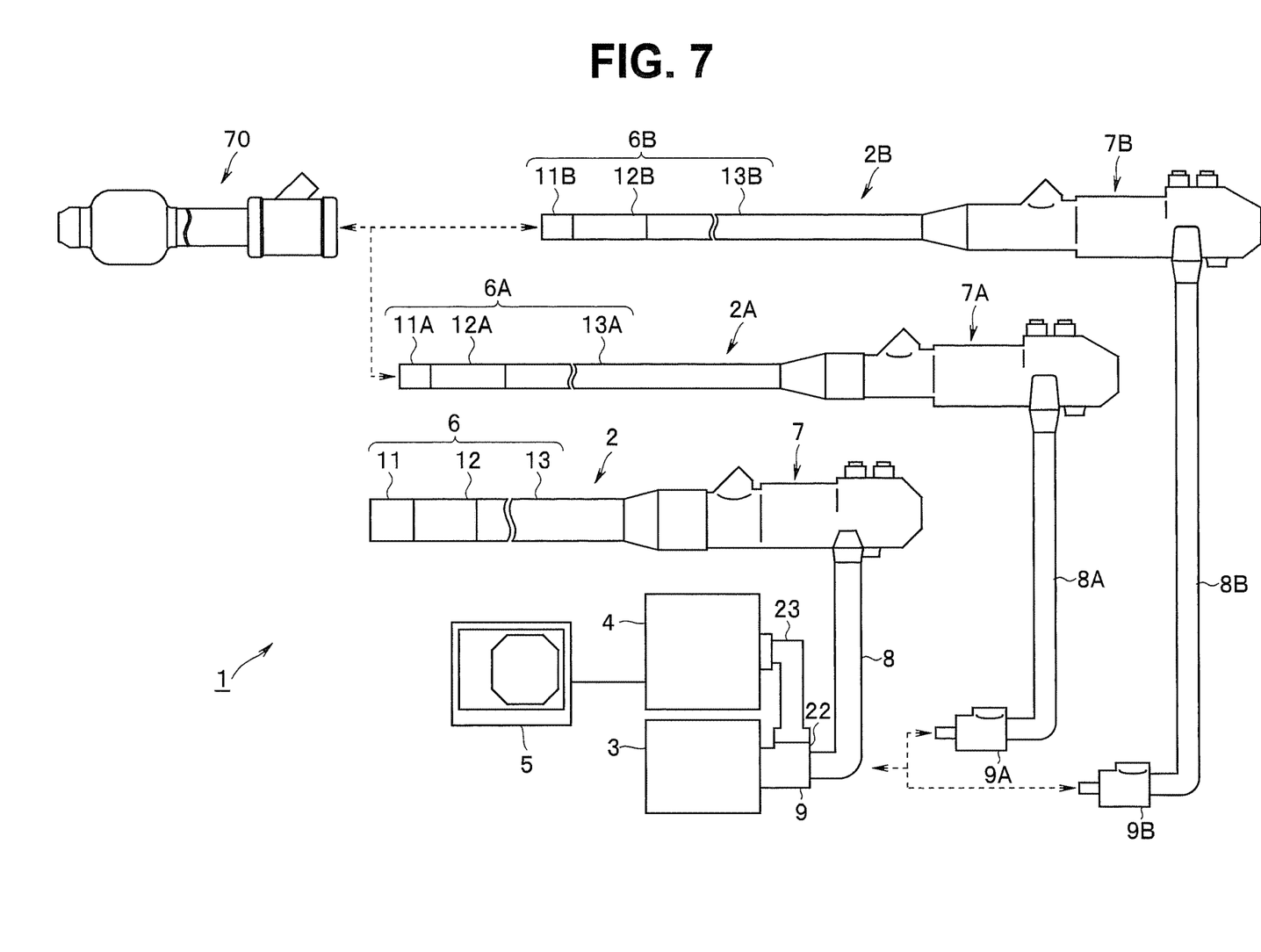
FIG. 7 relates to a second embodiment of the present invention and is a schematic configuration diagram of an endoscope system.

As shown in FIG. 7, in the second embodiment, an endoscope 2B functioning as a third endoscope is included in the endoscope system 1 in addition to the endoscopes 2 and 2A functioning as the first and second endoscopes and the over-tube 70. Like the endoscopes 2 and 2A, the endoscope 2B includes an elongated insertion section (a third insertion section) 6B, an operation section 7B, a universal cable 8B, and a connector 9B but does not include the hardness changing mechanism included in the endoscopes 2 and 2A.

In the endoscope 2B, an outer diameter of the insertion section 6B (a distal end portion 11B, a bending section 12B, and a flexible tube section 13B) is set to a diameter smaller than the outer diameter of the insertion section 6 (the distal end portion 11, the bending section 12, and the flexible tube section 13) of the endoscope 2 and smaller than the inner diameter of the over-tube 70. Therefore, like the endoscope 2A, the over-tube 70 can be attached to the endoscope 2B. A hardness characteristic of the endoscope 2B is set to be the hardness characteristic shown in FIG. 8.

As in the first embodiment, based on the endoscope 2 in which the over-tube 70 is not used, in the endoscope 2B, hardness of the insertion section 6B is set such that hardness Ht at a time when the over-tube 70 is attached to the insertion section 6B is substantially equal to the maximum hardness Hmax1 of the insertion section 6 of the endoscope 2. In the endoscopes 2A and 2B, in FIG. 8, the maximum hardness Hmax2 of the insertion section 6A and hardness Hi of the insertion section 6B are set substantially the same.

Figure 8:
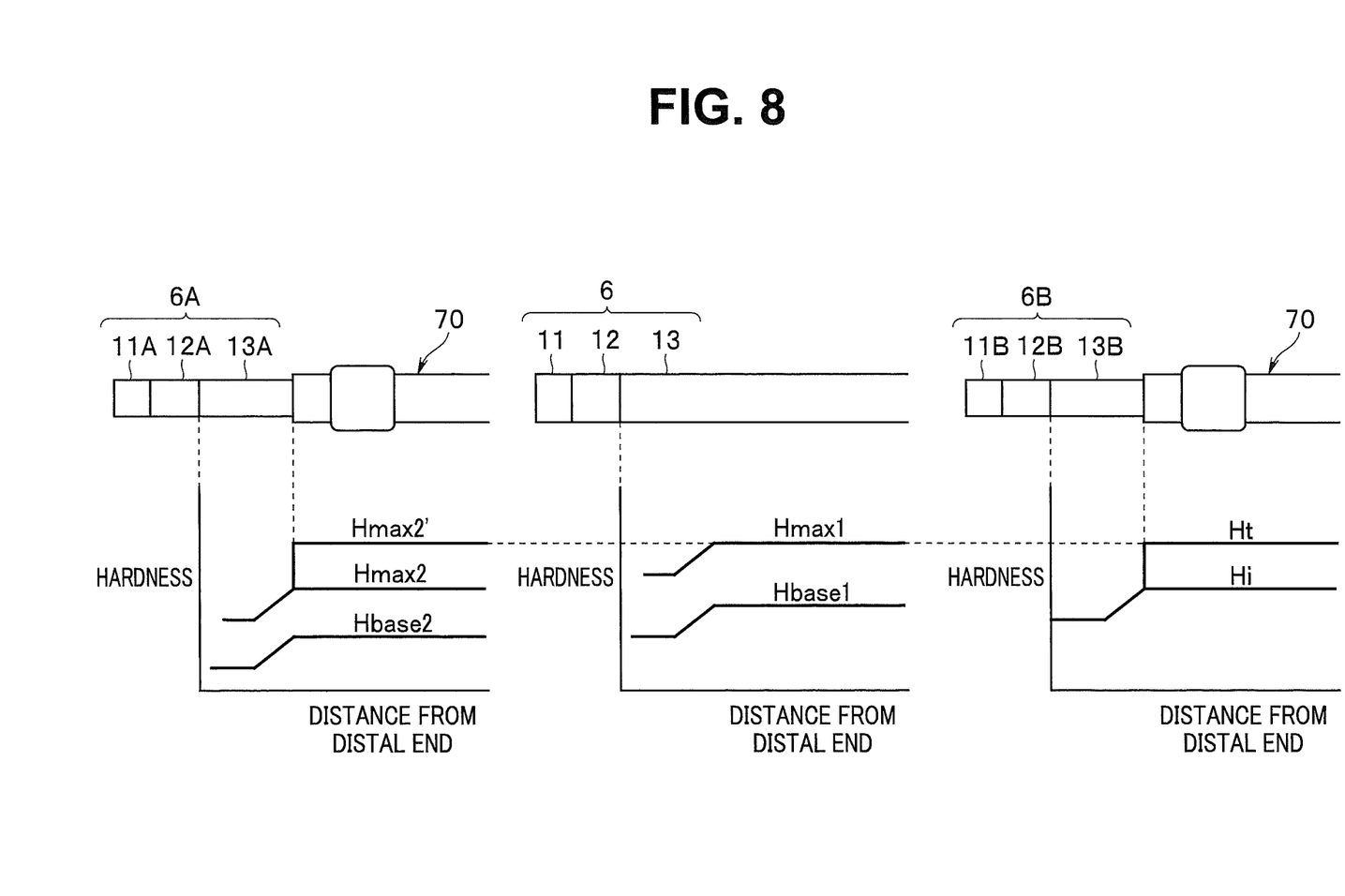
FIG. 8 relates to the second embodiment of the present invention and is an explanatory diagram showing hardness characteristics of insertion sections.

In this case, in the endoscope 2B not including the hardness changing mechanism, compared with the endoscopes 2 and 2A including the hardness changing mechanism, a degree of freedom of hardness setting of the insertion section is low. Therefore, the maximum hardnesses Hmax1 and Hmax2 of the endoscopes 2 and 2A may be adjusted on the basis of the hardness Ht at a time when the over-tube 70 is attached to the endoscope 2B. That is, the endoscopes 2 and 2A are respectively set such that the maximum hardness Hmax1 of the insertion section 6 of the endoscope 2 and the maximum hardness Hmax2 of the insertion section 6A of the endoscope 2A decrease by the hardness of the over-tube 70 with respect to the hardness Ht.

In the second embodiment, the maximum hardnesses of the insertion sections are set substantially equal in the endoscope 2 that includes the hardness changing mechanism but to which the over-tube 70 is not attached, the endoscope 2A that includes the hardness changing mechanism and to which the over-tube 70 is attached, and the endoscope 2B that does not include the hardness changing mechanism and to which the over-tube 70 is attached. Consequently, it is possible to achieve the same convenience of use in a plurality of endoscopes having different functions and obtain satisfactory insertability and operability.

What is claimed is:

1. An endoscope system comprising:
a first endoscope including a first insertion section formed to be elongated and a first hardness changing mechanism configured to change hardness of the first insertion section according to an operation on a first hand side of the first endoscope; and
a second endoscope including a second insertion section formed to be elongated and a second hardness changing mechanism configured to change hardness of the second insertion section according to an operation on a second hand side of the second endoscope, an over-tube being attachable to an outer circumference of the second insertion section,
the first hardness changing mechanism comprising:
a first elongated towing wire that, when pulled, contracts the first insertion section; and
a first towing member that pulls the first towing wire, the first towing member being operatively connected to a first hardness adjustment member provided on the first hand side of the first endoscope,
the second hardness changing mechanism comprising:
a second elongated towing wire that, when pulled, contracts the second insertion section; and
a second towing member that pulls the second towing wire, the second towing member being operatively connected to a second hardness adjustment member provided on the second hand side of the second endoscope,
the first endoscope and the second endoscope being selectively usable, wherein
a combined maximum hardness of the second insertion section of the second endoscope and the over-tube attached thereto is set substantially equal to or lower than a maximum hardness of the first insertion section of the first endoscope.

2. The endoscope system according to claim 1, wherein an outer diameter of the second insertion section in the second endoscope is set smaller than an outer diameter of the first insertion section in the first endoscope.

3. The endoscope system according to claim 1, wherein an outer diameter of the over-tube is set substantially equal to an outer diameter of the first insertion section in the first endoscope.

* * * * *